*(12)* United States Patent
Urfig (10) Patent No.: US 9,999,565 B2
(45) Date of Patent: Jun. 19, 2018

(54) STEAM SHOWER SYSTEM AND DEVICE

(71) Applicant: Bernard E. Urfig, Los Angeles, CA (US)

(72) Inventor: Bernard E. Urfig, Los Angeles, CA (US)

( * ) Notice: Subject to any disclaimer, the term of this patent is extended or adjusted under 35 U.S.C. 154(b) by 1 day.

(21) Appl. No.: 15/091,492

(22) Filed: Apr. 5, 2016

(65) Prior Publication Data

US 2016/0287471 A1    Oct. 6, 2016

Related U.S. Application Data

(60) Provisional application No. 62/178,234, filed on Apr. 6, 2015.

(51) Int. Cl.
*A61H 33/06* (2006.01)
*B05B 1/18* (2006.01)
*E03C 1/04* (2006.01)
*A61M 21/00* (2006.01)

(52) U.S. Cl.
CPC ........... *A61H 33/06* (2013.01); *A61H 33/066* (2013.01); *B05B 1/18* (2013.01); *E03C 1/0408* (2013.01); *A61H 2033/061* (2013.01); *A61H 2033/062* (2013.01); *A61H 2201/102* (2013.01); *A61H 2201/5046* (2013.01); *A61H 2201/5048* (2013.01); *A61H 2201/5097* (2013.01); *A61M 2021/0016* (2013.01)

(58) Field of Classification Search
CPC .... A61H 33/06; A61H 33/065; A61H 33/066; A61H 2003/061; A61H 2003/062; A61H 2003/068; A61H 2201/102

USPC ... 4/524, 525, 533, 535, 536, 537, 598, 601, 4/605, 597
See application file for complete search history.

(56) References Cited

U.S. PATENT DOCUMENTS

| | | | |
|---|---|---|---|
| 3,847,159 A | * | 11/1974 | Hofer ...................... B05B 1/267 239/507 |
| 3,857,514 A | | 12/1974 | Clifton |
| 3,945,881 A | | 3/1976 | Speidel |
| 4,084,271 A | | 4/1978 | Ginsberg |
| 4,424,598 A | | 1/1984 | Cima |
| 4,432,103 A | | 2/1984 | Hunziker |
| 4,685,221 A | | 8/1987 | Taylor et al. |
| 5,142,713 A | | 9/1992 | Makool |

(Continued)

FOREIGN PATENT DOCUMENTS

| | | | | |
|---|---|---|---|---|
| JP | 05038356 A | * | 2/1993 | ............ A61H 33/10 |
| JP | 05285188 A | * | 11/1993 | |

(Continued)

*Primary Examiner* — Erin Deery
(74) *Attorney, Agent, or Firm* — Olav M. Underdal; IDP Patent Services (57) ABSTRACT

A steam shower system, includes a steam enclosure, including a front plate, a rear wall, and a steam chamber; a steam mixing valve with a steam control dial; a mixed water line; a steam nozzle assembly with a stem nozzle head; a steam vent, including a perimeter wall, including a perimeter wall and a perimeter ledge; a steam deflector; a steam barrier; a vacuum air vent, which is optionally hidden behind the steam control dial; and aromatherapy device, including an aromatherapy aperture and receptor with a container for aromatic liquid; such that the steam vent is configured to emit steam from the steam chamber.

22 Claims, 10 Drawing Sheets

(56) References Cited

U.S. PATENT DOCUMENTS

| | | |
|---|---|---|
| 5,211,813 A | 5/1993 | Sawley et al. |
| 5,293,653 A | 3/1994 | Filipponi |
| 5,435,020 A * | 7/1995 | Maskell ............. A61H 33/06 |
| | | 4/524 |
| 5,551,637 A | 9/1996 | Lo |
| 5,713,309 A | 2/1998 | Higashi |
| 5,788,160 A | 8/1998 | Woog |
| 5,805,765 A | 9/1998 | Altman |
| 5,870,975 A * | 2/1999 | Luc ................. A61H 33/063 |
| | | 122/39 |
| 8,070,138 B2 * | 12/2011 | Saitou ............. A61H 33/063 |
| | | 261/28 |
| 8,646,121 B2 | 2/2014 | Nguyen |
| 2005/0241058 A1 | 11/2005 | Li |
| 2006/0208104 A1 | 9/2006 | DeBoer et al. |
| 2006/0248640 A1 | 11/2006 | Leong |
| 2007/0147808 A1 | 6/2007 | Egeresi |
| 2008/0184478 A1 | 8/2008 | Howard |

FOREIGN PATENT DOCUMENTS

| | | | |
|---|---|---|---|
| JP | 06233804 A | * | 8/1994 |
| JP | 06245976 A | * | 9/1994 |

\* cited by examiner

FIG. 2

Steam Shower System

Wireless/Bluetooth Sound Module

FIG. 11

Aromatherapy Device

FIG. 12

STEAM SHOWER SYSTEM AND DEVICE

CROSS-REFERENCE TO RELATED APPLICATIONS

This application claims the benefit of U.S. Provisional Application No. 62/178,234, filed Apr. 6, 2015.

FIELD OF THE INVENTION

The present invention relates generally to the field of showers and shower devices, and more particularly to methods and systems for generating steam in a shower.

BACKGROUND OF THE INVENTION

Steam showers have become increasingly common in recent years.

However, such steam shower and wet saunas are often complex and expensive, and may require electrical power for operation. Designs that rely solely on hot and cold water supply frequently do not generate sufficient steam and may emit unwanted drops and spouts of hot water, and therefore have not been successful in the market place.

As such, considering the foregoing, it may be appreciated that there continues to be a need for novel and improved devices and methods for generating steam in a shower.

SUMMARY OF THE INVENTION

The foregoing needs are met, to a great extent, by the present invention, wherein in aspects of this invention, enhancements are provided to the existing model of steam showers.

In an aspect, a steam shower system can include:
a) a steam enclosure, including a front plate; a rear wall; and a steam chamber within walls of the steam enclosure;
b) a mixed water line, which is connected to a hot and cold water supply, such that mixed water is transmitted via the mixed water line;
c) a steam nozzle assembly, including at least one steam nozzle head; such that the steam nozzle head is configured to spray the mixed water onto the rear wall at a nozzle inclination angle, whereby the mixed water is partially atomized into a steam;
d) a steam vent, with a steam aperture, which is configured as an aperture in the front plate, such that the steam vent is configured to emit the steam from the steam chamber.

In a related aspect, the steam shower system can further include a steam mixing valve, with a steam control dial.

In a related aspect, the steam shower system can further include a steam deflector, which is mounted inside the steam enclosure, such that the steam deflector is configured to protrude from the rear wall at a deflector inclination angle; whereby the steam deflector is configured to deflect and direct the steam, towards the steam vent.

In a related aspect, the steam shower system can further include a steam barrier, which is a plate that is mounted to an inner side of the steam enclosure, wherein the steam barrier comprises barrier apertures, which are configured to form a partial barrier to stop a flow of the steam downwards towards a lower end of the steam chamber, while allowing excess water to drip or flow through the barrier apertures, such that the excess water can flow towards the lower end of the steam chamber.

In a related aspect, the steam shower system can further include a vacuum air vent, which is an aperture in the steam enclosure; wherein the vacuum air vent is configured to enable an airflow from the vacuum air vent to the steam vent, which facilitates creation of a continuous and directed stream of the steam exiting the steam vent.

There has thus been outlined, rather broadly, certain embodiments of the invention in order that the detailed description thereof herein may be better understood, and in order that the present contribution to the art may be better appreciated. There are, of course, additional embodiments of the invention that will be described below and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of embodiments in addition to those described and of being practiced and carried out in various ways. In addition, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

DETAILED DESCRIPTION

Before describing the invention in detail, it should be observed that the present invention resides primarily in a novel and non-obvious combination of elements and process steps. So as not to obscure the disclosure with details that will readily be apparent to those skilled in the art, certain conventional elements and steps have been presented with lesser detail, while the drawings and specification describe in greater detail other elements and steps pertinent to understanding the invention.

The following embodiments are not intended to define limits as to the structure or method of the invention, but only to provide exemplary constructions. The embodiments are permissive rather than mandatory and illustrative rather than exhaustive.

Figure 1:
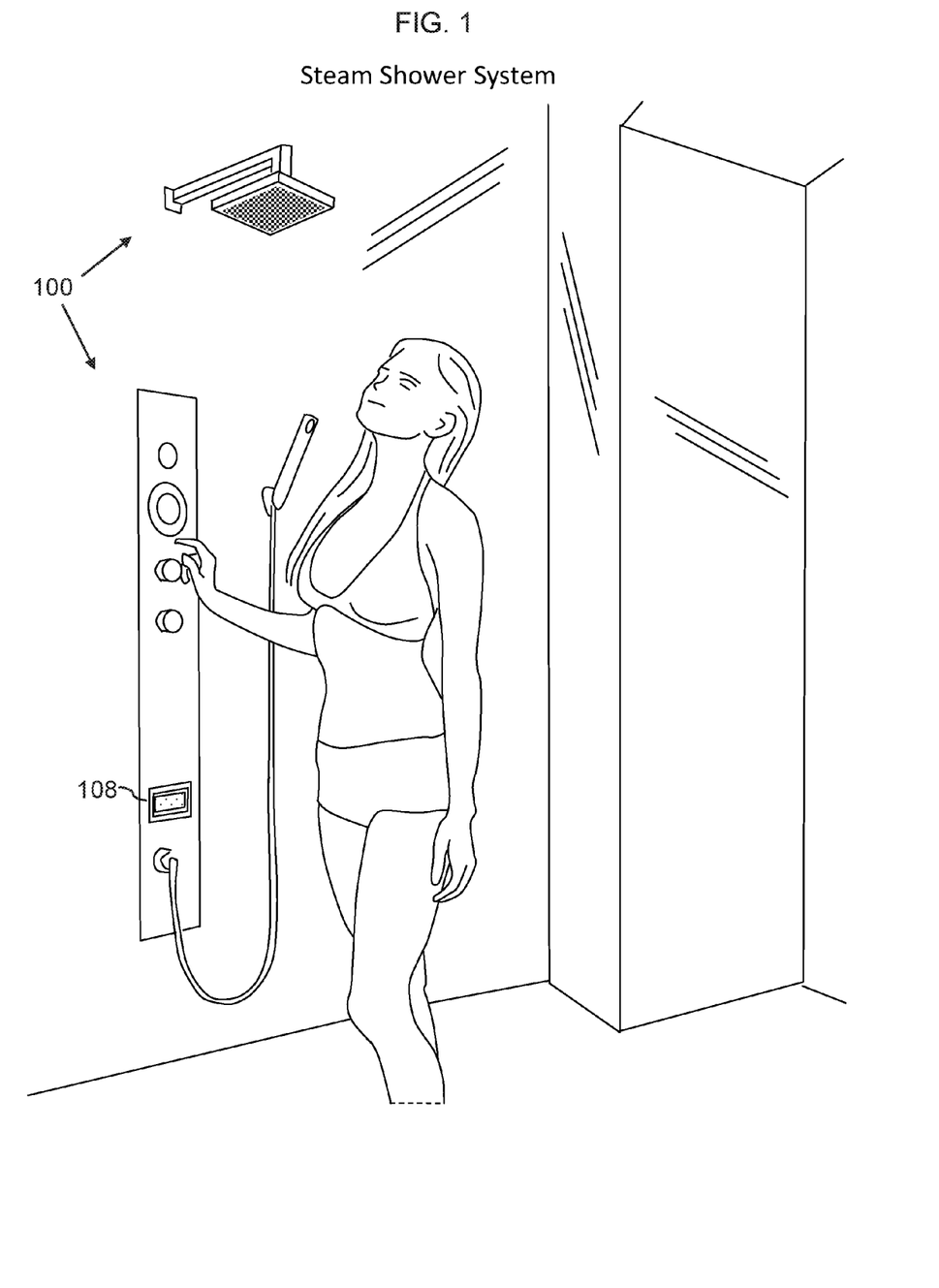
FIG. 1 is a perspective view of a steam shower system, according to an embodiment of the invention.

In an embodiment, a steam shower system 100, such as shown in FIG. 1, can be designed to provide a home owner, hotel or alike the ability to enjoy the benefits of a steam shower without having to use a generator or electricity, and also have the ability to install it far easier than other known steam shower systems.

In related embodiments, the steam shower system 100 can function as a steam and complete shower system 100, designed to vent steam and heat into a shower enclosure, through a steam vent 108, thereby creating a steam shower, also known as a wet sauna. As well as providing a unique steam shower, the steam shower system 100 incorporates a complete shower system which can add other luxurious features such as a rainfall shower head, body sprays, and a BLUETOOTH™ audio system for a one of a kind shower experience.

In further related embodiments, the steam shower system 100:
a) Provides all functions of a state-of-the-art luxurious shower, combined into one beautifully designed system;
b) Allows easy installation by a qualified plumber or contractor with minimal installation complexity and cost; and
c) Can be constructed entirely from high grade stainless steel, incorporating a modern, and beautiful design that will enhance a bathroom's appearance.

Figure 2:
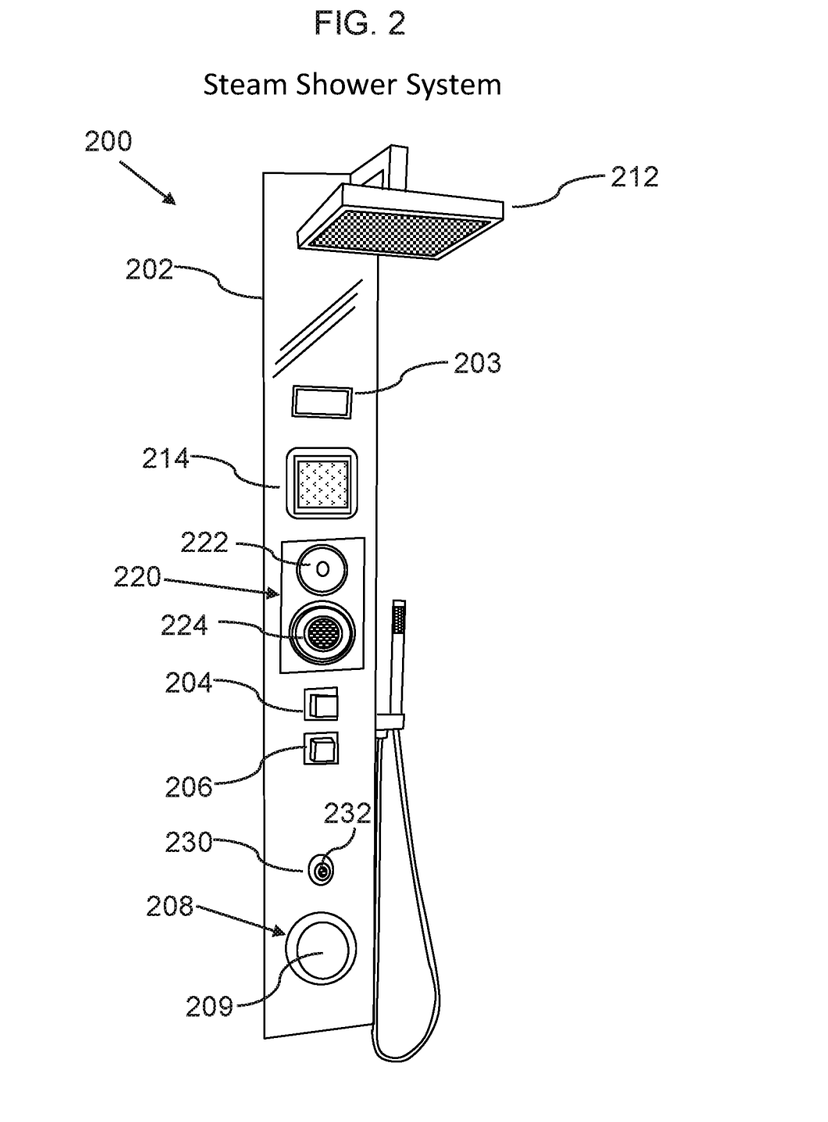
FIG. 2 is a perspective view of a steam shower system, according to an embodiment of the invention.

In an embodiment, as shown in FIG. 2, a steam shower system 200 can include:
a) a shower head 212, which as shown can be a rainfall shower head 212;
b) a front plate 202;
c) a vacuum air vent 203;
d) a secondary shower head 214, which as shown can be a back and shoulder shower head 214;
e) a wireless sound module 220, which can be a BLUETOOTH™ sound module 220; which can further include:
  i. a sound control module 222; and
  ii. at least one speaker 224;
f) a shower control dial 204, further including a water mixer which mixes water from cold and hot water supply and transmits water to the shower head 212 and the secondary shower head 214;
g) a steam control dial 206;
h) an aromatherapy device 230, which includes an aromatherapy aperture 232;
i) a steam vent 208, comprising a steam aperture 209, which is configured as an aperture in the front plate 202, such that the steam vent 208 is configured to emit steam that is generated in a steam chamber behind the front plate 202.

Figure 3:
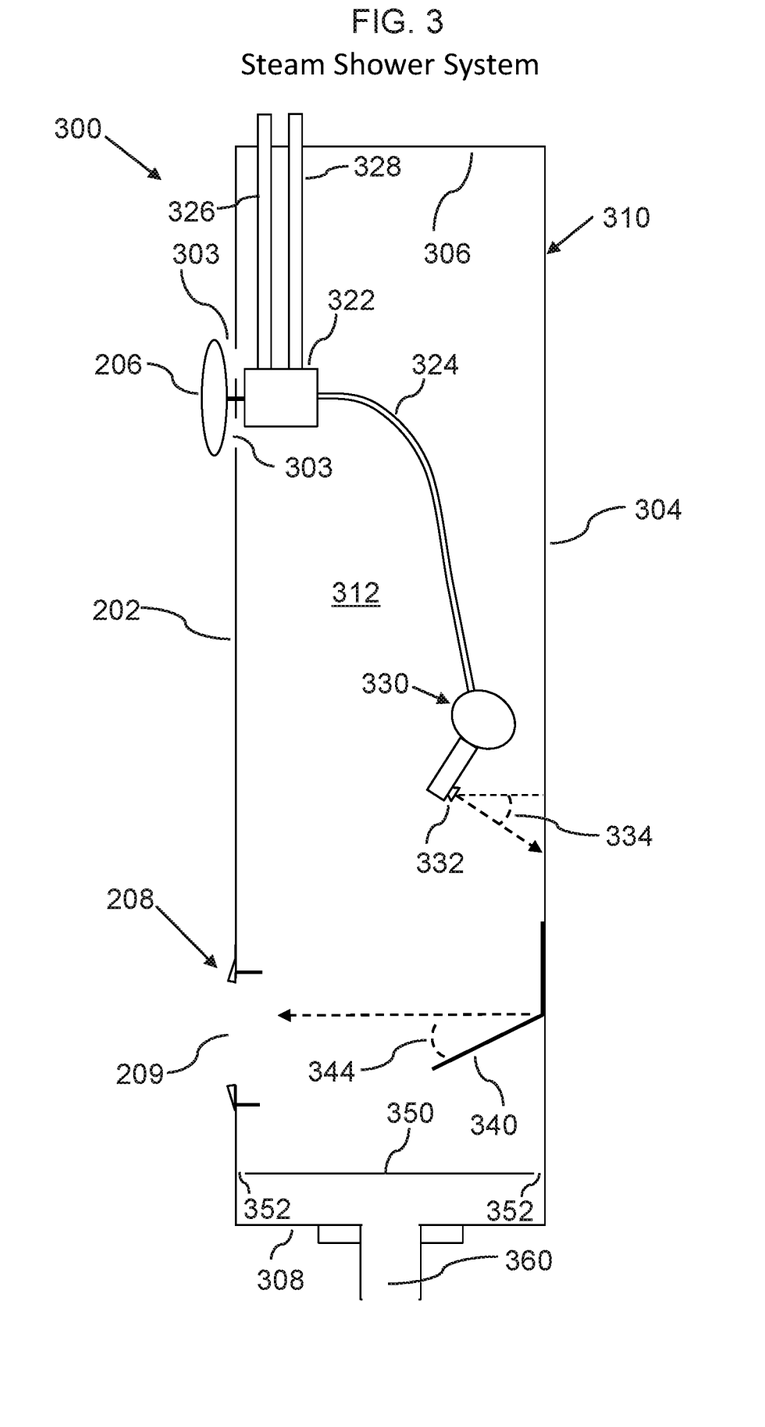
FIG. 3 is a schematic cross-sectional view of a steam shower system, according to an embodiment of the invention.

In a related embodiment, FIG. 3 illustrates a schematic view of the steam shower system 300, showing components configured to generate steam, such that the steam shower system 200, includes:
a) a steam enclosure 310, including:
  i. a front plate 202; a rear wall 304; an upper wall 306, a lower wall 308, and sidewalls (not visible, in plane of FIG. 3);
  ii. a steam chamber 312; which is a cavity within the enclosure formed by the front plate 202; rear wall 304; upper wall, a lower wall, and sidewalls;
b) a mixed water line 324;
c) a steam mixing valve 322, which is connected to a hot and cold water supply 326 328, such that the mixing valve further includes:
  iii. the steam control dial 206, configured such that adjustment of the steam control dial 206, adjusts mixing of hot and cold water from the hot and cold water supply, such that mixed water is transmitted to the mixed water line 324;
d) a steam nozzle assembly 330, including:
  iv. at least one steam nozzle head 332;
    wherein the at least one steam nozzle head 332 is connected to the mixed water line 324; such that the steam nozzle head is configured to spray the mixed water onto the rear wall 304 at a nozzle inclination angle 334
e) a steam deflector 340 which is configured to protrude from the rear wall 304 at a deflector inclination angle 344, such that the steam deflector 340 is configured to deflect and direct steam, from the steam nozzle head 332, such the steam is direct towards the steam vent 208;
f) a steam barrier 350, which is a plate that is mounted to an inner side of the steam enclosure 310, below the steam deflector 340 and above the drain 360, such that the steam barrier 350 is substantially perpendicular to side walls of the steam enclosure 310, and is configured to form a partial barrier to stop a flow of steam downwards towards the drain 360, while allowing excess water to drip or flow through at least one barrier aperture 352, such that the excess water can flow through the drain 360.

In a related embodiment, the steam shower system 200 is configured to separate the steam from the water, such that the steam exits via the steam vent 208, to a shower user, and the water goes down the drain 360, which is connected to an external drain line, or can also be directed anywhere away from the shower including simply to an outside outlet, if there is no drain access.

In a related embodiment, the steam shower system 300 can function as a stand-alone system, for delivering steam only, or the steam shower system 300 can be part of a full steam shower system 100 200.

In a related embodiment, the at least one barrier apertures 352 can be formed as at least one gap between the steam barrier and a sidewall of the steam enclosure 310.

In other embodiments, all sides of the steam barrier 350 can be connected to side walls of the steam enclosure 310, such that there are no gaps between the steam barrier 350 and a sidewall of the steam enclosure 310, such that the at least one barrier aperture 352 is one or a plurality of apertures in the steam barrier 350.

In a related embodiment, as shown in FIG. 3, the vacuum air vent 303 can be configured behind the shower control dial 204, the steam control dial 206, or another control dial or panel feature, such that the vacuum air vent 303 is hidden.

In a related embodiment, the nozzle inclination angle 334 can be in a range of 45-60 degrees, 35-70 degrees, or a larger range of 0-90 degrees.

In a related embodiment, the deflector inclination angle 344 can be in a range of 6-20 degree, 4-35 degrees, or in a larger range between 0 and 90 degrees.

In a related example embodiment, the nozzle inclination angle 334 can be substantially 54 degrees, and the deflector inclination angle 344 can be substantially 12 degrees, whereby the steam is deflected by the steam deflector 340 such that a direction of the steam is perpendicular to a plane of the front plate 202, when the steam exits through the steam vent 208.

In a further related embodiment, the vacuum air vent 203 functions to allow an airflow from the vacuum air vent 203 to the steam vent 208, which facilitates creation of a continuous and directed stream of steam exiting the steam vent 208, whereby the flow of steam and hot air is raised to the level of a "Fan-type" of force, which blows hot air and steam out through the steam vent 208.

In a further related embodiment, the steam shower system 100 200 is configured to create an internal water flow, such that the steam shower system 100 200 creates a vacuum, wherein the water turbulence creates a suction of air flow, which allows air to enter via the vacuum air vent 203 and the steam to exit the chamber via the steam vent 208.

In a further related embodiment, the steam barrier 350 functions to prevent an airflow from the steam chamber 312 to the drain 360, which facilitates creation of a continuous and directed stream of steam exiting the steam vent 208.

In a further related embodiment, the steam nozzle assembly 330 can be positioned below the vacuum air vent 303.

In a further related embodiment, the steam nozzle assembly 330 can be positioned above the steam deflector 340 and the steam vent 208.

In a further related embodiment, the steam barrier 350 can be positioned below the steam deflector 340 and the steam vent 208, and above the drain 360.

Figure 4:
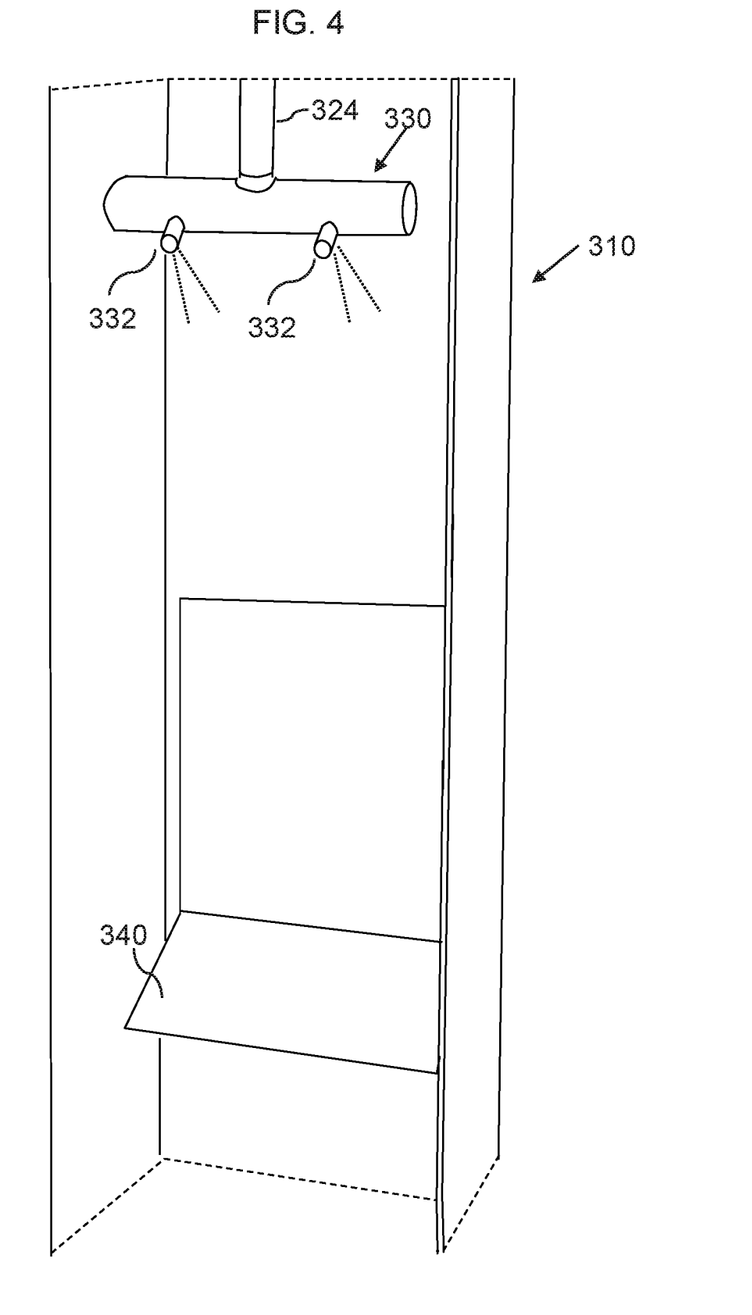
FIG. 4 is a front perspective view of inside parts of the steam shower system, according to an embodiment of the invention.

In a related embodiment, FIG. 4 illustrates a variant of the steam nozzle assembly 330, with two steam nozzle heads 332, as installed inside the steam enclosure 310.

Figure 5:
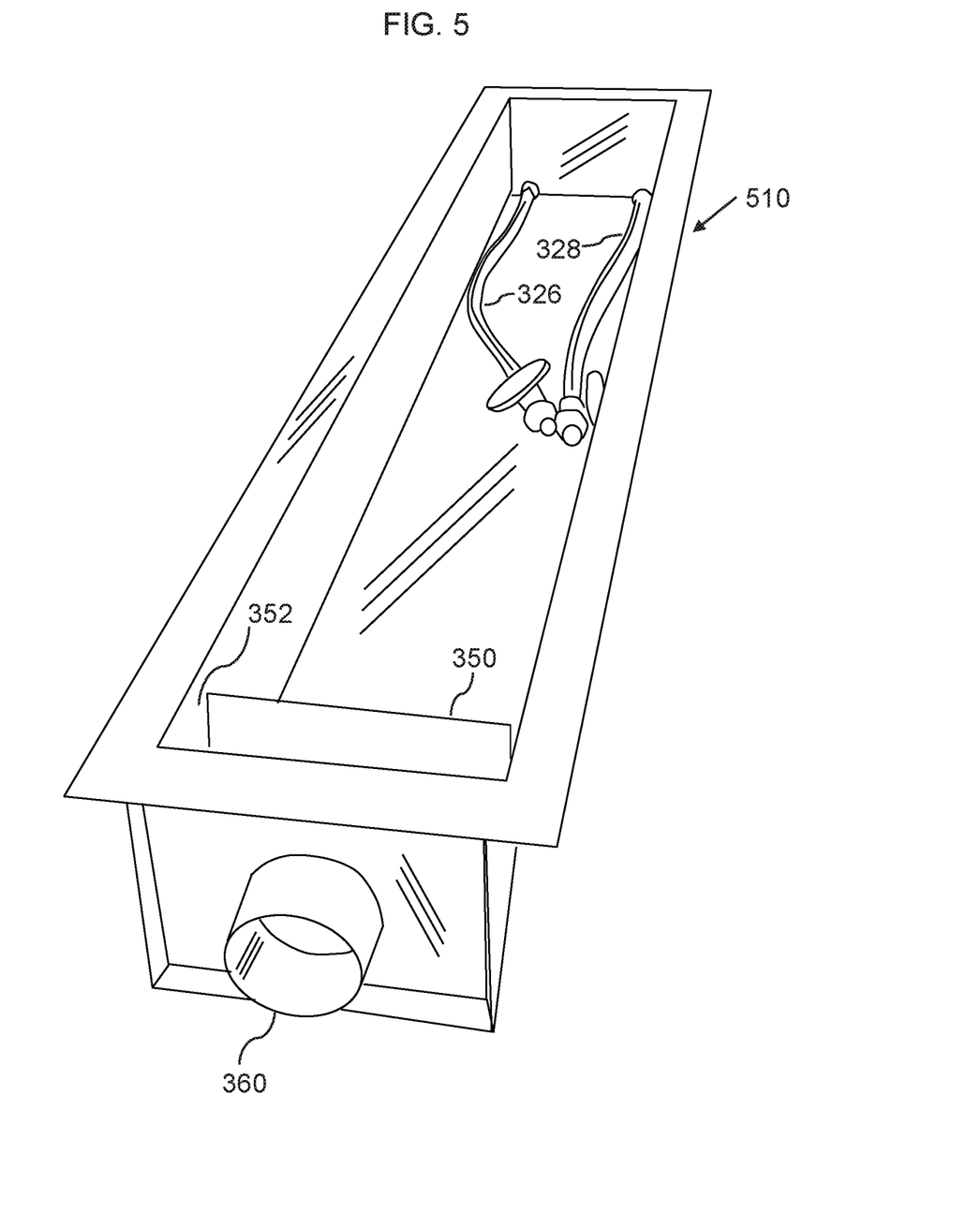
FIG. 5 is a bottom perspective view of a steam enclosure, according to an embodiment of the invention.

In a related embodiment, FIG. 5 illustrates a bottom perspective view of the steam enclosure 510 without the front plate 202, showing the drain 360 and the steam barrier 350, wherein the steam enclosure 510 can be connected to the water supply lines and drain 360.

Figure 6:
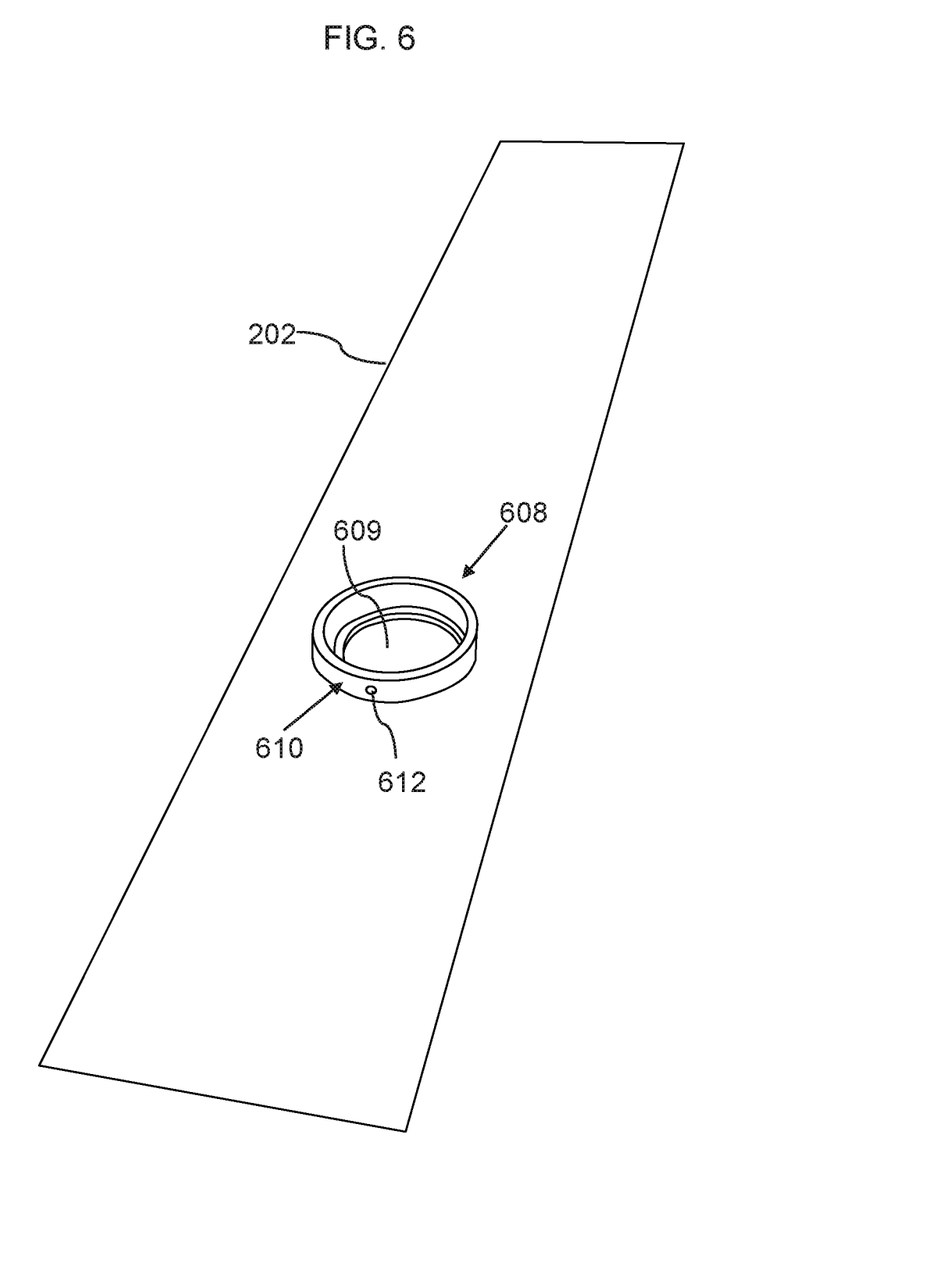
FIG. 6 is a perspective view of an inner side of a front plate, according to an embodiment of the invention.

In a related embodiment, as shown in FIG. 6, the steam vent 608 can further include a perimeter wall 610, which is mounted on an inner side of the front plate 202, such that the perimeter wall 610 surrounds the steam aperture 609 of the steam vent 608, whereby the perimeter wall 610 directs steam through the steam aperture 609 of the steam vent 608. The perimeter wall 610 can further include a perimeter aperture 612 in a lower part of the perimeter wall, which is configured to allow drainage of water that accumulates inside the perimeter wall 610. The perimeter wall 610 can for example have a height of ⅝ inch, with the perimeter aperture 612 having a diameter of ⅛ inch.

Figure 7:
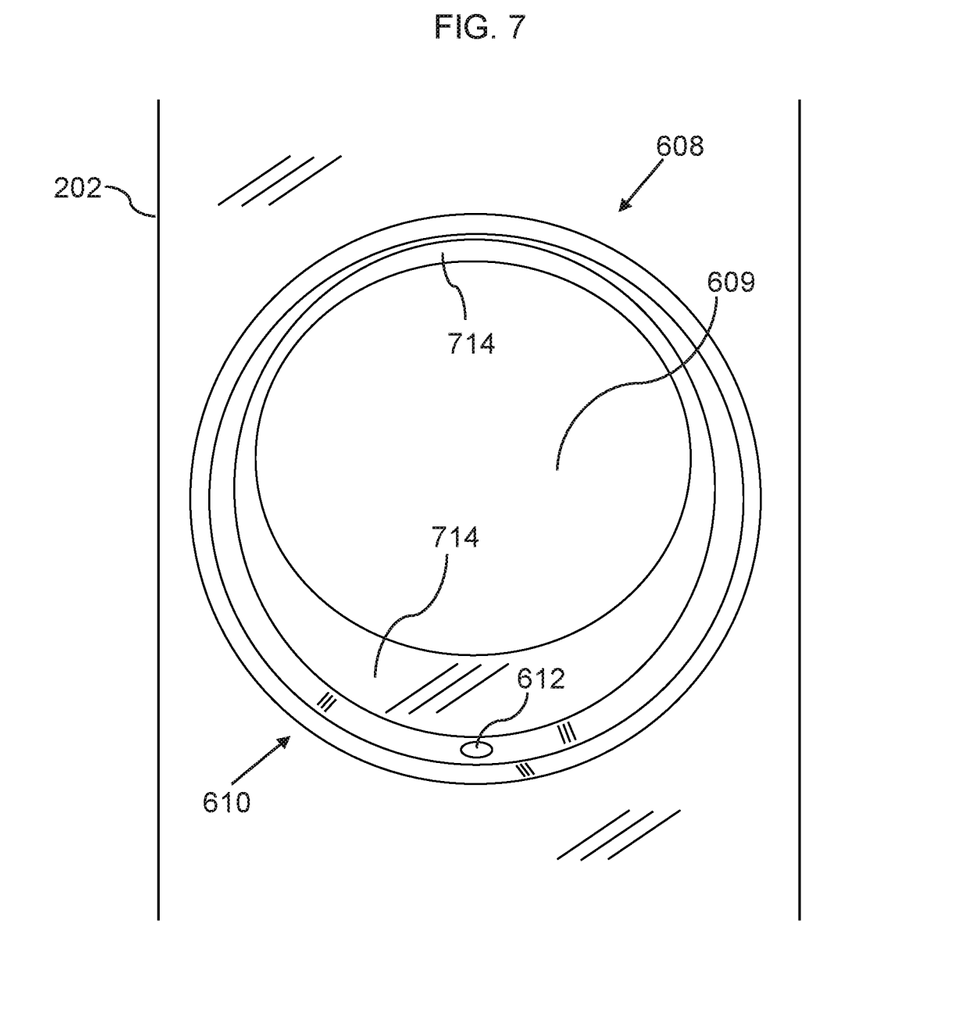
FIG. 7 is a perspective view of an inner side of a steam vent, according to an embodiment of the invention.

In a further related embodiment, as shown in FIG. 7, the perimeter wall 610, can have a larger diameter than the steam aperture 609 of the steam vent 608, such that a steam ledge 714 is formed, which is a part of the inner side of the front plate 202, inside the perimeter wall 610. The steam ledge 714 serves to prevent water drops to pass through the steam aperture 609.

In a yet further related embodiment, as further shown in FIG. 7, the perimeter wall 610, can be positioned off-center with respect to the steam aperture 609, such that the steam ledge 714 is wider below the steam aperture 609 than above the steam aperture 609. Water may tend to accumulate inside the lower part of the perimeter wall 610, and is allowed to drain away through the perimeter aperture 612.

Figure 11:
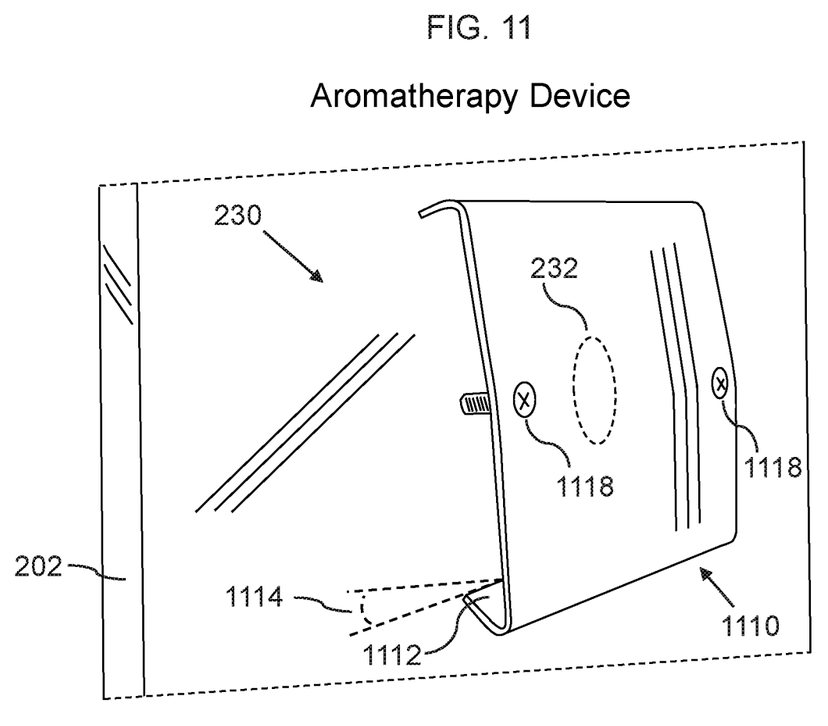
FIG. 11 is a rear perspective view of an aromatherapy device mounted on an inner side of a front plate of a steam shower system, according to an embodiment of the invention.
Figure 12:
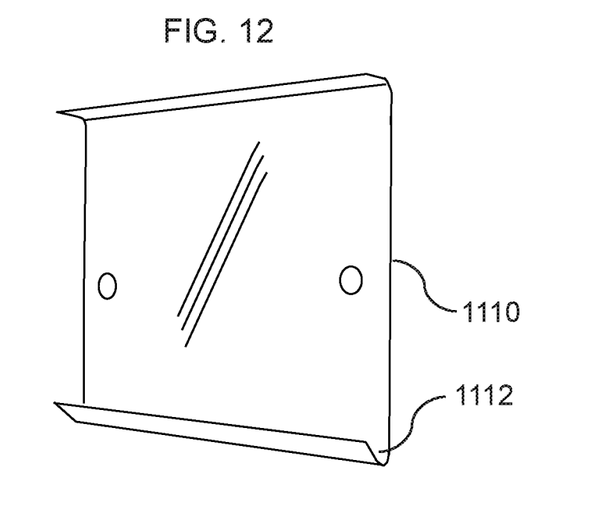
FIG. 12 is a front perspective view of an aromatherapy device, according to an embodiment of the invention.

In a related embodiment, as shown in FIGS. 11 and 12, the aromatherapy device 230, can include:
 a. an aromatherapy aperture 232, which is an aperture in the front plate 202; and
 b. an aromatherapy receptor 1110, including:
  i. an aroma container 1112, which is configured to receive an aromatic liquid, such as an aromatic oil, which is injected though the aromatherapy aperture 232;
   wherein the aromatherapy receptor 1110 is mounted on an inner side of the front plate 202, for example with screws 1118, such that the aromatic liquid will drip from the aroma container and become dispersed in the steam and water within the steam chamber 312.

In a further related embodiment, as shown in FIGS. 11 and 12, the aromatherapy receptor 1110 can be configured with a j-shaped lower part, which protrudes towards the front plate 202, such that the aroma container 1112 is configured as a u-shaped channel 1112 with open ends, whereby an aromatic oil, which is injected though the aromatherapy aperture 232, will be received by the u-shaped channel 1112, and will slowly drip from the open ends.

In a yet further related embodiment, as shown in FIG. 11, the aromatherapy receptor 1110 can be mounted with an inclination angle 1114, such that the aromatic liquid will drip from the lower end of the u-shaped channel 1112. The inclination angle 1114 can for example be configured in a range of 0-20 degrees, 1-5 degrees, 1-10 degrees, or 1-20 degrees. A lower inclination angle 1114 will produce a slower dispersion of the aromatic liquid.

Figure 8:
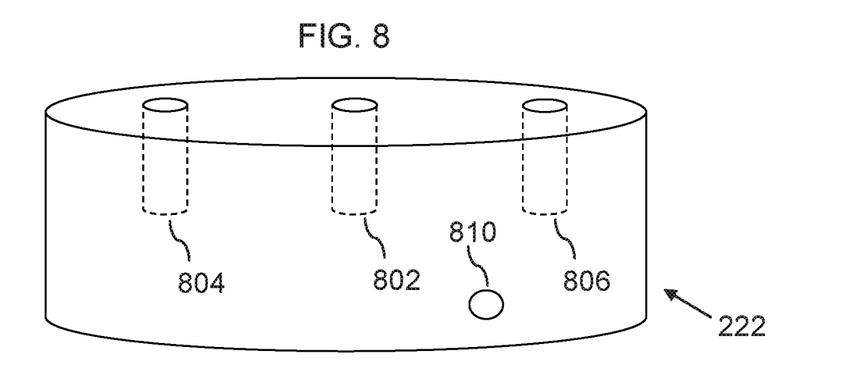
FIG. 8 is a perspective view of a wireless sound module, according to an embodiment of the invention.
Figure 9:
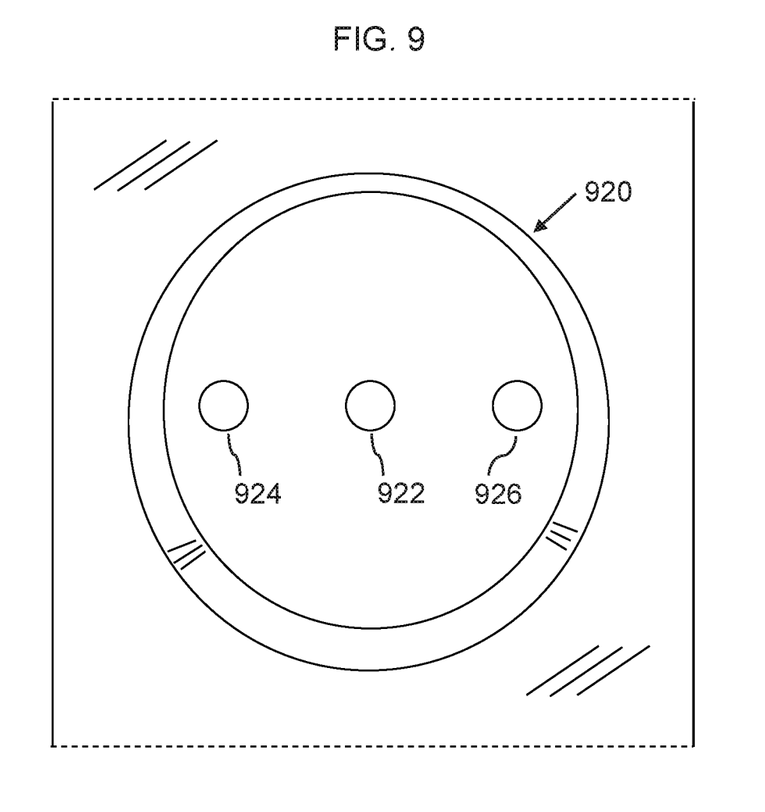
FIG. 9 is a front view of a sound module cavity, according to an embodiment of the invention.

In a related embodiment, as shown in FIGS. 8 and 9, the wireless sound module 220 can be configured with a removable sound control module 222, which can be inserted into a control module receptor 920, which is a cavity in the front plate 202 or in a front plate of the wireless sound module 220

In a further related embodiment, the wireless sound module 220 can further include a module magnet 802, on an inner side of the wireless sound module 220, which is configured to connect to a corresponding cavity magnet 922 inside the control module receptor 920, such that the module magnet 802 and the cavity magnet 922 are held together by magnetism when connected.

In a further related embodiment, the wireless sound module 220 can further include module speaker connectors 804 806, on an inner side of the wireless sound module 220, which is configured to connect to corresponding cavity speaker connectors 924 926 inside the control module receptor 920, such that an amplified speaker signal is transmitted via the module speaker connectors 804 806 and the corresponding cavity speaker connectors 924 926 when they are connected, such that the cavity speaker connectors 924 926 are connected to the speaker 224.

In a yet further related embodiment, the module speaker connectors 804 806 and the corresponding cavity speaker connectors 924 926 can be configured to be magnetized, such that they are held together by magnetism when connected. Further, the module speaker connectors 804 806 and the cavity speaker connectors 924 926, can be nickel plated rare earth magnets, such that current flows substantially in the nickel plating.

Figure 10:
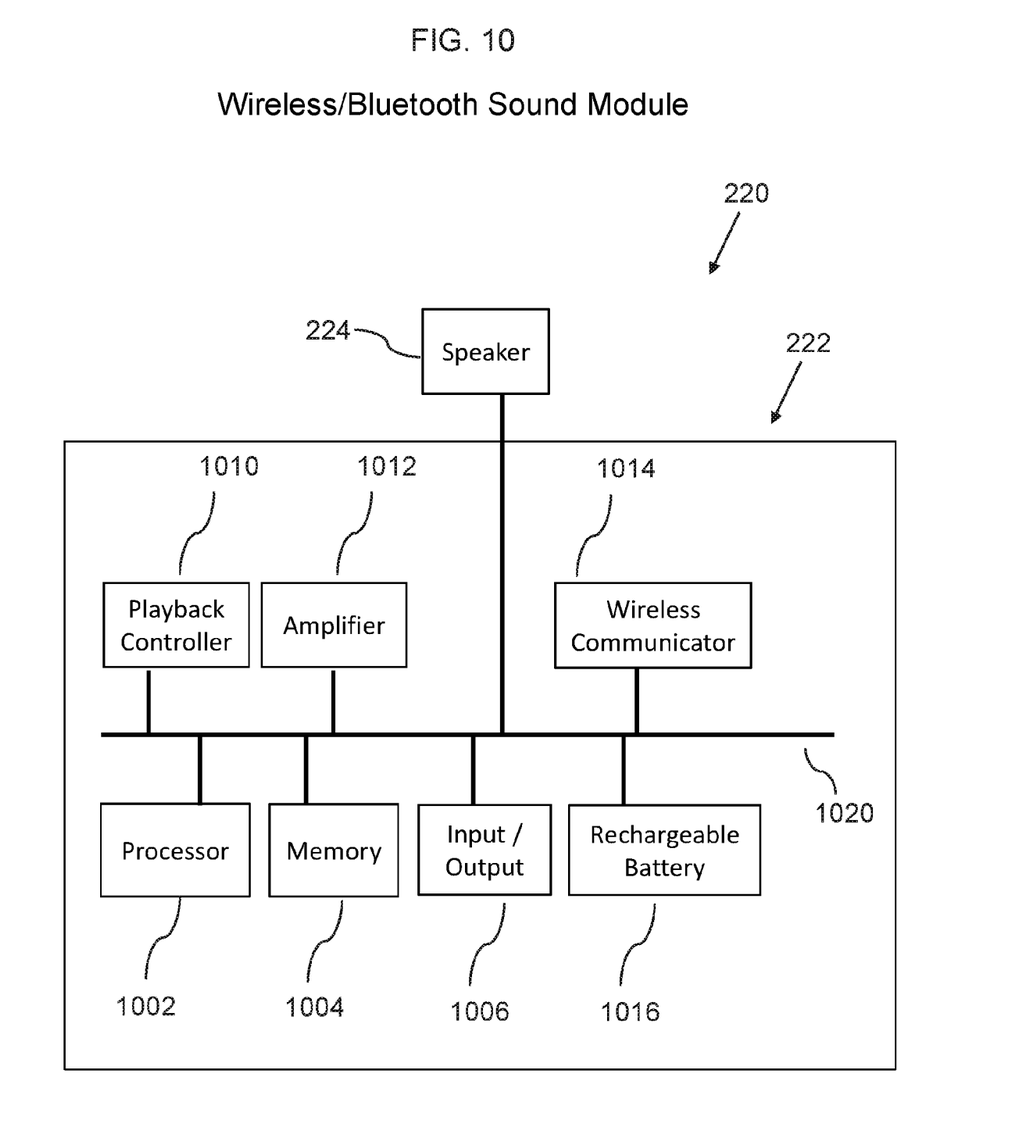
FIG. 10 is a schematic diagram illustrating a wireless sound module, according to an embodiment of the invention.

In a related embodiment, a sound control module 222 can include:

a) A processor 1002;

b) A non-transitory memory 1004;

c) An input/output component 1006, which can include playback control keys on a front of the sound control module;

d) A playback controller 1010; which is configured to control playback of audio received via the wireless communicator 1014;

e) An amplifier 1012, which is configured to receive audio via the wireless communicator 1014;

f) A wireless communicator 1014, which is configured to receive audio via a wireless connection to a mobile device or other wireless audio source, wherein the wireless connection can communicate over BLUETOOTH™, WIFI, or other wireless communication protocol;

g) A rechargeable battery 1016, which is configured to provide power to the sound control module 222, such that the rechargeable battery 1016 is connected to the charging port 810, such that the rechargeable battery 1016 can be recharged when the sound control module 222 is removed from the control module receptor 920; all connected via h) A data and power bus 1020.

FIG. 10 represents a block diagram, device, system, apparatus, and computer program product according to various embodiments of the present invention. It shall be understood that each block or step of the block diagram, flowchart and control flow illustrations, and combinations of blocks in the block diagram, flowchart and control flow illustrations, can be implemented by computer program instructions or other means. Although computer program instructions are discussed, an apparatus or system according to the present invention can include other means, such as hardware or some combination of hardware and software, including one or more processors or controllers, for performing the disclosed functions.

In this regard, FIG. 10 depicts the computer devices of various embodiments, each containing several of the key components of a general-purpose computer by which an embodiment of the present invention may be implemented. Those of ordinary skill in the art will appreciate that a computer can include many components. However, it is not necessary that all of these generally conventional components be shown in order to disclose an illustrative embodiment for practicing the invention. The general-purpose computer can include a processing unit and a system memory, which may include various forms of non-transitory storage media such as random access memory (RAM) and read-only memory (ROM). The computer also may include nonvolatile storage memory, such as a hard disk drive, where additional data can be stored.

It shall be understood that the above-mentioned components of the sound control module 222 are to be interpreted in the most general manner.

For example, the processor 1002 can include a single physical microprocessor or microcontroller, a cluster of processors, a datacenter or a cluster of datacenters, a computing cloud service, and the like.

In a further example, the non-transitory memory 1004 can include various forms of non-transitory storage media, including random access memory and other forms of dynamic storage, and hard disks, hard disk clusters, cloud storage services, and other forms of long-term storage. Similarly, the input/output 1006 can include a plurality of well-known input/output devices, such as screens, keyboards, pointing devices, motion trackers, communication ports, and so forth.

Furthermore, it shall be understood that the sound control module 222 can include a number of other components that are well known in the art of general computer devices, and therefore shall not be further described herein. This can include system access to common functions and hardware, such as for example via operating system layers such as WINDOWS™, LINUX™, and similar operating system software, but can also include configurations wherein application services are executing directly on server hardware or via a hardware abstraction layer other than a complete operating system.

An embodiment of the present invention can also include one or more input or output components, such as a mouse, keyboard, monitor, and the like. A display can be provided for viewing text and graphical data, as well as a user interface to allow a user to request specific operations. Furthermore, an embodiment of the present invention may be connected to one or more remote computers via a network interface. The connection may be over a local area network (LAN) wide area network (WAN), and can include all of the necessary circuitry for such a connection.

In a related embodiment, the sound control module 222 communicates with a mobile device or other computer device over a wireless network, which can include Wi-Fi, BLUETOOTH™, ZIGBEE™, and NFC.

Typically, computer program instructions may be loaded onto the computer or other general-purpose programmable machine to produce a specialized machine, such that the instructions that execute on the computer or other programmable machine create means for implementing the functions specified in the block diagrams, schematic diagrams or flowcharts. Such computer program instructions may also be stored in a computer-readable medium that when loaded into a computer or other programmable machine can direct the machine to function in a particular manner, such that the instructions stored in the computer-readable medium produce an article of manufacture including instruction means that implement the function specified in the block diagrams, schematic diagrams or flowcharts.

In addition, the computer program instructions may be loaded into a computer or other programmable machine to cause a series of operational steps to be performed by the computer or other programmable machine to produce a computer-implemented process, such that the instructions that execute on the computer or other programmable machine provide steps for implementing the functions specified in the block diagram, schematic diagram, flowchart block or step.

Accordingly, blocks or steps of the block diagram, flowchart or control flow illustrations support combinations of means for performing the specified functions, combinations of steps for performing the specified functions and program instruction means for performing the specified functions. It will also be understood that each block or step of the block diagrams, schematic diagrams or flowcharts, as well as combinations of blocks or steps, can be implemented by special purpose hardware-based computer systems, or combinations of special purpose hardware and computer instructions, that perform the specified functions or steps.

As an example, provided for purposes of illustration only, a data input software tool of a search engine application can be a representative means for receiving a query including one or more search terms. Similar software tools of applications, or implementations of embodiments of the present invention, can be means for performing the specified functions. For example, an embodiment of the present invention may include computer software for interfacing a processing element with a user-controlled input device, such as a mouse, keyboard, touch screen display, scanner, or the like. Similarly, an output of an embodiment of the present invention may include, for example, a combination of display software, video card hardware, and display hardware. A processing element may include, for example, a controller or microprocessor, such as a central processing unit (CPU), arithmetic logic unit (ALU), or control unit.

Here has thus been described a multitude of embodiments of the steam shower system 100 200, and devices and methods related thereto, which can be employed in numerous modes of usage.

The many features and advantages of the invention are apparent from the detailed specification, and thus, it is intended by the appended claims to cover all such features and advantages of the invention, which fall within the true spirit and scope of the invention.

Many such alternative configurations are readily apparent, and should be considered fully included in this specification and the claims appended hereto. Accordingly, since numerous modifications and variations will readily occur to those skilled in the art, it is not desired to limit the invention to the exact construction and operation illustrated and described, and thus, all suitable modifications and equivalents may be resorted to, falling within the scope of the invention.

What is claimed is:

1. A steam shower system, comprising:
   a) a steam enclosure, comprising:
      a front plate;
      a rear wall;
      a plurality of sidewalls; and
      a steam chamber, which is a cavity within the steam enclosure;
   b) a mixed water line, which is configured to connect to a water supply, such that mixed water is transmitted via the mixed water line;
   c) a steam nozzle assembly, comprising:
      at least one steam nozzle head;
      wherein the steam nozzle assembly is mounted inside the steam enclosure;
      wherein the at least one steam nozzle head is connected to the mixed water line; such that the steam nozzle head is configured to spray the mixed water onto the rear wall at a nozzle inclination angle;
      whereby the mixed water is partially atomized into a steam; and
   d) a steam vent, comprising:
      a steam aperture, disposed in the front plate, such that the steam vent is configured to emit the steam from the steam chamber; and
      a perimeter wall, which is mounted on an inner side of the front plate, such that the perimeter wall surrounds the steam aperture of the steam vent, whereby the perimeter wall directs steam through the steam aperture.

2. The steam shower system of claim 1, further comprising:
   a steam mixing valve, comprising:
      a steam control dial;
   wherein the steam mixing valve is configured to connect to the water supply; and the steam mixing valve is configured such that adjustment of the steam control dial adjusts mixing of hot and cold water from the water supply, such that the mixed water is transmitted to the mixed water line.

3. The steam shower system of claim 1, further comprising:
   a steam deflector, which is mounted inside the steam enclosure, such that the steam deflector is configured to protrude from the rear wall at a deflector inclination angle;
   whereby the steam deflector is configured to deflect and direct the steam, towards the steam vent.

4. The steam shower system of claim 3, wherein the deflector inclination angle is configured in a range of 4-35 degrees.

5. The steam shower system of claim 3, wherein the nozzle inclination angle is 54 degrees, and the deflector inclination angle is 12 degrees.

6. The steam shower system of claim 3, further comprising:
   a steam barrier, which is a plate that is mounted to an inner side of the steam enclosure, below the steam deflector, such that the steam barrier is substantially perpendicular to the plurality of sidewalls of the steam enclosure, wherein the steam barrier comprises:
      at least one barrier aperture
   wherein the steam barrier is configured to form a partial barrier to stop a flow of the steam downwards towards a lower end of the steam chamber, while allowing excess water to drip or flow through the at least one barrier aperture, such that the excess water can flow towards the lower end of the steam chamber.

7. The steam shower system of claim 6, wherein the at least one barrier aperture comprises at least one gap between the steam barrier and one of the group consisting of the front plate, the rear wall, and one of the plurality of sidewalls of the steam enclosure.

8. The steam shower system of claim 1, wherein the nozzle inclination angle is configured in a range of 35-70 degrees.

9. The steam shower system of claim 1, further comprising:
   a vacuum air vent, which is an aperture in the steam enclosure;
   wherein the vacuum air vent is configured to enable an airflow from the vacuum air vent to the steam vent, which facilitates creation of a continuous and directed stream of the steam exiting the steam vent.

10. The steam shower system of claim 9, wherein the vacuum air vent is above the steam vent.

11. The steam shower system of claim 9, further comprising:
   a steam mixing valve, including:
      a steam control dial,
   wherein the steam mixing valve is configured to connect to the water supply; and the steam mixing valve is configured such that adjustment of the steam control dial adjusts mixing of hot and cold water from the water supply, such that the mixed water is transmitted to the mixed water line;
   wherein the vacuum air vent is configured to be behind the steam control dial, such that the vacuum air vent is hidden behind the steam control dial.

12. The steam shower system of claim 1, wherein the perimeter wall further comprises:
   a perimeter aperture, which is positioned in a lower part of the perimeter wall;

such that the perimeter aperture is configured to allow drainage of water that accumulates inside the perimeter wall.

13. The steam shower system of claim 1, wherein the perimeter wall is configured with a larger diameter than a diameter of the steam aperture, such that a steam ledge is formed, the steam ledge formed by a part of the inner side of the front plate that is inside the perimeter wall;
whereby the steam ledge serves to prevent water drops from passing through the steam aperture.

14. The steam shower system of claim 13, wherein the perimeter wall is positioned off-center with respect to the steam aperture, such that the steam ledge is wider below the steam aperture than above the steam aperture.

15. The steam shower system of claim 1, further comprising:
an aromatherapy device, comprising:
an aromatherapy aperture, which is an aperture in the front plate; and
an aromatherapy receptor, comprising:
an aroma container, which is configured to receive an aromatic liquid, which is injected though the aromatherapy aperture;
wherein the aromatherapy receptor is attached on an inner side of the front plate;
such that the aromatic liquid drips from the aroma container;
whereby the aromatic liquid is dispersed in the steam within the steam chamber.

16. The steam shower system of claim 15, wherein the aromatherapy receptor is configured with a j-shaped lower part, which protrudes towards the front plate, such that the aroma container is configured as a u-shaped channel with open ends, whereby the aromatic oil is received by the u-shaped channel and drips from the open ends, when the aromatic oil is injected though the aromatherapy aperture.

17. The steam shower system of claim 16, wherein the aromatherapy receptor is mounted with an inclination angle, such that the aromatherapy receptor is configured to enable the aromatic liquid to drip from a lower end of the u-shaped channel.

18. The steam shower system of claim 17, wherein the inclination angle is in a range of 1-20 degrees.

19. The steam shower system of claim 1, further comprising a drain, which is an aperture in a lower end of the steam enclosure.

20. A steam shower system, comprising:
a) a steam enclosure, comprising:
a front plate;
a rear wall;
a plurality of sidewalls; and
a steam chamber, which is a cavity within the steam enclosure;
b) a mixed water line, which is configured to connect to a water supply, such that mixed water is transmitted via the mixed water line;
c) a steam nozzle assembly, comprising:
at least one steam nozzle head;
wherein the steam nozzle assembly is mounted inside the steam enclosure;
wherein the at least one steam nozzle head is connected to the mixed water line; such that the steam nozzle head is configured to spray the mixed water onto the rear wall at a nozzle inclination angle;
whereby the mixed water is partially atomized into a steam;
d) a steam vent, comprising a steam aperture, disposed in the front plate, such that the steam vent is configured to emit the steam from the steam chamber;
e) a steam deflector, which is mounted inside the steam enclosure, such that the steam deflector is configured to protrude from the rear wall at a deflector inclination angle;
whereby the steam deflector is configured to deflect and direct the steam, towards the steam vent; and
f) a steam barrier, which is a plate that is mounted to an inner side of the steam enclosure, below the steam deflector, such that the steam barrier is substantially perpendicular to the plurality of sidewalls of the steam enclosure, wherein the steam barrier comprises:
at least one barrier aperture
wherein the steam barrier is configured to form a partial barrier to stop a flow of the steam downwards towards a lower end of the steam chamber, while allowing excess water to drip or flow through the at least one barrier aperture, such that the excess water can flow towards the lower end of the steam chamber.

21. A steam shower system, comprising:
a) a steam enclosure, comprising:
a front plate;
a rear wall;
a plurality of sidewalls; and
a steam chamber, which is a cavity within the steam enclosure;
b) a mixed water line, which is configured to connect to a water supply, such that mixed water is transmitted via the mixed water line;
c) a steam nozzle assembly, comprising:
at least one steam nozzle head;
wherein the steam nozzle assembly is mounted inside the steam enclosure;
wherein the at least one steam nozzle head is connected to the mixed water line; such that the steam nozzle head is configured to spray the mixed water onto the rear wall at a nozzle inclination angle;
whereby the mixed water is partially atomized into a steam;
d) a steam vent, comprising a steam aperture, disposed in the front plate, such that the steam vent is configured to emit the steam from the steam chamber;
e) a vacuum air vent, which is an aperture in the steam enclosure;
wherein the vacuum air vent is configured to enable an airflow from the vacuum air vent to the steam vent, which facilitates creation of a continuous and directed stream of the steam exiting the steam vent; and
f) a steam mixing valve, including:
a steam control dial,
wherein the steam mixing valve is configured to connect to the water supply; and
the steam mixing valve is configured such that adjustment of the steam control dial adjusts mixing of hot and cold water from the water supply, such that the mixed water is transmitted to the mixed water line;
wherein the vacuum air vent is configured to be behind the steam control dial, such that the vacuum air vent is hidden behind the steam control dial.

22. A steam shower system, comprising:
a) a steam enclosure, comprising:
a front plate;
a rear wall;

a plurality of sidewalls; and
a steam chamber, which is a cavity within the steam enclosure;
b) a mixed water line, which is configured to connect to a water supply, such that mixed water is transmitted via the mixed water line;
c) a steam nozzle assembly, comprising:
at least one steam nozzle head;
wherein the steam nozzle assembly is mounted inside the steam enclosure;
wherein the at least one steam nozzle head is connected to the mixed water line; such that the steam nozzle head is configured to spray the mixed water onto the rear wall at a nozzle inclination angle;
whereby the mixed water is partially atomized into a steam;
d) a steam vent, comprising a steam aperture, disposed in the front plate, such that the steam vent is configured to emit the steam from the steam chamber; and
e) an aromatherapy device, comprising:
an aromatherapy aperture, which is an aperture in the front plate; and
an aromatherapy receptor, comprising:
an aroma container, which is configured to receive an aromatic liquid, which is injected though the aromatherapy aperture;
wherein the aromatherapy receptor is attached on an inner side of the front plate;
such that the aromatic liquid drips from the aroma container;
whereby the aromatic liquid is dispersed in the steam within the steam chamber.

* * * * *